(12) United States Patent
Taub et al.

(10) Patent No.: US 9,539,071 B2
(45) Date of Patent: Jan. 10, 2017

(54) METHOD AND SYSTEM FOR DESIGNING AND PRODUCING DENTAL PROSTHESES AND APPLIANCES

(71) Applicant: Align Technology, Inc., San Jose, CA (US)

(72) Inventors: Eldad Taub, Reut (IL); Avi Kopelman, Palo Alto, CA (US)

(73) Assignee: Align Technology, Inc., San Jose, CA (US)

( * ) Notice: Subject to any disclaimer, the term of this patent is extended or adjusted under 35 U.S.C. 154(b) by 446 days.

(21) Appl. No.: 14/061,598

(22) Filed: Oct. 23, 2013

(65) Prior Publication Data

US 2014/0142736 A1   May 22, 2014
US 2016/0354185 A9   Dec. 8, 2016

Related U.S. Application Data

(63) Continuation of application No. 13/399,866, filed on Feb. 17, 2012, now Pat. No. 8,577,493, which is a continuation of application No. 12/789,573, filed on May 28, 2010, now Pat. No. 8,145,340, which is a continuation of application No. 12/007,015, filed on Jan. 4, 2008, now Pat. No. 7,738,989, which is a continuation of application No. 11/062,622, filed on Feb. 23, 2005, now Pat. No. 7,333,874.

(Continued)

(51) Int. Cl.
| | | |
|---|---|---|
| A61C 13/00 | (2006.01) | |
| A61C 5/10 | (2006.01) | |
| A61C 7/00 | (2006.01) | |
| A61C 8/00 | (2006.01) | |
| A61C 13/09 | (2006.01) | |

(52) U.S. Cl.
CPC ............. *A61C 13/0004* (2013.01); *A61C 5/10* (2013.01); *A61C 13/0006* (2013.01); *A61C 7/002* (2013.01); *A61C 8/0048* (2013.01); *A61C 13/09* (2013.01); *Y10T 29/49567* (2015.01)

(58) Field of Classification Search
None
See application file for complete search history.

(56) References Cited

U.S. PATENT DOCUMENTS

| 2,467,432 A | 4/1949 | Kesling |
|---|---|---|
| 3,407,500 A | 10/1968 | Kesling |

(Continued)

FOREIGN PATENT DOCUMENTS

| AU | 3031677 A | 5/1979 |
|---|---|---|
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.

(Continued)

*Primary Examiner* — Sean Shechtman
(74) *Attorney, Agent, or Firm* — Wilson Sonsini Goodrich & Rosati

(57) ABSTRACT

A virtual model of an intraoral cavity is provided, wherein this process is initialized by a dental clinic, and the design and manufacture of a suitable dental prosthesis for the intraoral cavity is shared between a dental lab and a service center.

20 Claims, 7 Drawing Sheets

Related U.S. Application Data

(60) Provisional application No. 60/546,946, filed on Feb. 24, 2004.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,398,554 B1 | 6/2002 | Perot et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,632,089 B2 | 10/2003 | Rubbert et al. |

(56) References Cited

U.S. PATENT DOCUMENTS

| | | | |
|---|---|---|---|
| 6,705,863 B2 | 3/2004 | Phan et al. | |
| 6,722,880 B2 | 4/2004 | Chishti et al. | |
| 6,786,726 B2 | 9/2004 | Lehmann et al. | |
| 6,882,894 B2 | 4/2005 | Durbin et al. | |
| 7,112,065 B2 | 9/2006 | Kopelman et al. | |
| 7,184,150 B2 | 2/2007 | Quadling et al. | |
| 7,333,874 B2 | 2/2008 | Taub et al. | |
| 7,363,239 B1 | 4/2008 | Andersson et al. | |
| 7,738,989 B2 | 6/2010 | Taub et al. | |
| 8,145,340 B2 | 3/2012 | Taub et al. | |
| 8,577,493 B2 | 11/2013 | Taub et al. | |
| 2002/0006597 A1 | 1/2002 | Andreiko et al. | |
| 2002/0013636 A1 | 1/2002 | O'Brien et al. | |
| 2003/0009252 A1 | 1/2003 | Pavlovskaia et al. | |
| 2003/0139834 A1 | 7/2003 | Nikolskiy et al. | |
| 2003/0222366 A1 | 12/2003 | Stangel et al. | |
| 2003/0224311 A1 | 12/2003 | Cronauer | |
| 2004/0128010 A1 | 7/2004 | Pavlovskaia et al. | |
| 2004/0220691 A1 | 11/2004 | Hofmeister et al. | |
| 2005/0055118 A1 | 3/2005 | Nikolskiy et al. | |
| 2005/0177266 A1 | 8/2005 | Kopelman et al. | |
| 2005/0186540 A1* | 8/2005 | Taub | A61O 5/10 433/223 |
| 2012/0239177 A1 | 9/2012 | Taub et al. | |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 1293174 A1 | 3/2003 |
| ES | 463897 | 1/1980 |
| FR | 2369828 A1 | 6/1978 |
| FR | 2525103 A1 | 10/1983 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 00/08415 A1 | 2/2000 |
| WO | WO 02/19940 A1 | 3/2002 |
| WO | WO 02/076326 A2 | 10/2002 |
| WO | WO 2004/008981 A2 | 1/2004 |
| WO | WO 2004/008981 A3 | 1/2004 |
| WO | WO 2004/087000 A1 | 10/2004 |

OTHER PUBLICATIONS

Alcaniz, et al. "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures, " AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Burstone et al., Precision Adjustment of the Transpalatal Lingual Arch: Computer Arch Form Predetermination, Am, Journal of Orthodontics, vol. 79, No. 2 (Feb. 1981), pp. 115-133.

(56) References Cited

OTHER PUBLICATIONS

Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," Am. J. Orthod., 73(1):36-46 (Jan. 1978).

Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.

(56) References Cited

OTHER PUBLICATIONS

Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993).
Proffit et al., Contemporary Orthodontics, (Second Ed.), Chapter 15, Mosby Inc., pp. 470-533 (Oct. 1993).
Raintree Essix & ARS Materials, Inc , Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, a Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Sinclair, "The Readers' Corner," J. Clin. Orthod., 26(6):369-372 (Jun. 1992).
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients html>, 2 pages (May 19, 2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.

(56) References Cited

OTHER PUBLICATIONS

Verstreken et al., "An Image-Guided Planning System for Endosseous Oral Implants," IEEE Trans. Med. Imaging, 17(5):842-852 (Oct. 1998).

Warunek et al., Physical and Mechanical Properties of Elastomers in Orthodonic Positioners, Am J. Orthod. Dentofac. Orthop, vol. 95, No. 5, (May 1989) pp. 399-400.

Warunek et.al., Clinical Use of Silicone Elastomer Applicances, JCO (1989) XXIII(10):694-700.

Wells, Application of the Positioner Appliance in Orthodontic Treatment, Am. J. Orthodont. (1970) 58:351-366.

Williams, "Dentistry and CAD/CAM: Another French Revolution," J. Dent. Practice Admin., pp. 2-5 (Jan./Mar. 1987).

Williams, "The Switzerland and Minnesota Developments in CAD/CAM," J. Dent. Practice Admin., pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).

Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances—Pro Lab product information for patients, 2 pages (2002).

\* cited by examiner

METHOD AND SYSTEM FOR DESIGNING AND PRODUCING DENTAL PROSTHESES AND APPLIANCES

CROSS-REFERENCE

This application is a continuation application of U.S. patent application Ser. No. 13/399,866, filed Feb. 17, 2012, which is a continuation application of U.S. patent application Ser. No. 12/789,573, filed May 28, 2010, now U.S. Pat. No. 8,145,340, which is a continuation application of U.S. patent application Ser. No. 12/007,015, filed Jan. 4, 2008, now U.S. Pat. No. 7,738,989, which is a continuation application of U.S. patent application Ser. No. 11/062,622, filed on Feb. 23, 2005, now U.S. Pat. No. 7,333,874, which claims the benefit under 35 USC §119(e) of U.S. Provisional Application No. 60/546,946, filed Feb. 24, 2004, the entire content of each of which is herein incorporated by reference.

FIELD OF THE INVENTION

This invention relates to methods and systems for designing and producing dental prostheses and appliances, and to dental prostheses and appliances produced thereby. In particular, the present invention is concerned with such systems in which a plurality of different work centers linked to a dental clinic utilize a common 3D database each for planning, designing and manufacturing at least parts of such prostheses and appliances.

BACKGROUND OF THE INVENTION

A dental treatment often begins with obtaining a three-dimensional (3D) model of a patient's teeth. The model may be a physical model of the dentition or a virtual 3D computer model. The model is used to assist in designing a dental treatment for the patient. After the treatment has been designed, the model is used to design the dental prosthesis or appliance to be applied to the teeth in order to execute the treatment. Such prostheses and appliances include, for example, bridges, crowns, and orthodontic braces.

In some instances, a negative cast of the dentition is obtained at the dental clinic in which the patient is seen, and may include both arches, one arch, or part of an arch. The cast is sent to a dental laboratory, and a positive physical model of the dentition is made from the negative cast, typically by pouring plaster into the cast allowing the plaster to set. A dental treatment is then determined at the clinic using the model, and prostheses or appliances for mounting onto the patient's teeth are designed or selected in order to execute the treatment. The appliances are made at a laboratory and then dispatched to the clinic for mounting onto the patient's teeth.

It is also known to obtain a 3D virtual representation of the teeth that is used to assist in devising a dental treatment and/or to design dental appliances. The 3D computer model may be obtained at the dental clinic using an optical scanner to scan the teeth directly or to scan a model of the teeth. The computer model is then used at the clinic for designing or selecting appropriate dental prosthesis and/or appliances to carry out the treatment. Instructions are then sent to a dental appliance laboratory for making the prosthesis or appliances, which are made at the laboratory and then dispatched to the clinic.

Alternatively, a negative cast of the dentition of each jaw is obtained at a dental clinic that is dispatched to a dental appliance laboratory where a 3D positive model of the patient's teeth is made from the negative cast. The 3D model is then scanned at the laboratory so as to generate a virtual 3D model of the patient's teeth that is used to design appropriate dental prosthesis or appliances. The prosthesis or appliances are produced at the laboratory and then dispatched to the clinic.

U.S. Pat. No. 6,632,089 to Rubbert et al., discloses a computer-based dental treatment planning method. A virtual 3D model of the dentition of a patient is obtained that is used to plan a dental treatment. Obtaining the 3D model as well as treatment planning can be performed at a dental clinic or at a remote location such as a dental appliance laboratory having access to the virtual model of the dentition. In the latter situation, the proposed treatment plan is sent to the clinic for review, and modification or approval by the dentist, before the requisite appliances are made at the laboratory.

SUMMARY OF THE INVENTION

The present invention provides a system and method for designing and producing dental prostheses, such as for example crowns and bridges. The system comprises at least one dental clinic and at least one dental laboratory. The system also comprises a dental service center that is a separate entity with respect to the dental laboratory. The service center is equipped to generate a virtual 3D model (also referred to herein as a "3D numerical model", "numerical model" "virtual model", and the like) of a patient's teeth from data obtained either by scanning (typically optically) the teeth directly or by scanning a physical model of the teeth, the process being at least initiated at the dental clinic. Alternatively, the dental lab may generate the virtual model. The service center is also equipped to use the computer model to design a dental treatment and to select or design and to manufacture dental prostheses, or at least a part thereof. The details of the required prosthesis may then be sent to the clinic, and typically part of the manufacture of the prosthesis is handled by the service center. The dental lab may also be equipped to design at least a part of the prosthesis, typically a coping, for example by first defining the finish line on the 3D model. Alternatively, the dental lab may provide a prescription to the service center for the latter to design the coping. The clinic may then send instructions to a dental laboratory and/or to the service center, each of which is equipped to make a part of the dental prosthesis in accordance with instructions and data received and/or generated from any one of the dental clinic, dental lab or from the service center, and the manufactured prosthesis is then dispatched to the clinic.

In a preferred embodiment, communication between the clinics, laboratories and the service center is over an electronic communications network such as the Internet or other suitable communications medium such as an intranet, local access network, public switched telephone network, cable network, etc.

At least a part of the manufacturing of the prosthesis is shared between the service center and one or more dental labs, according to predetermined criteria. Further, at least one of the service center and the at least one said dental lab is adapted for designing said prosthesis based on the 3D numerical model of the dentition, wherein said prosthesis comprises an inner surface and an outer surface, wherein to provide a 3D model of said prosthesis. The service center is adapted for manufacturing at least a first portion of said prosthesis based on said 3D numerical model. In particular, the service center is adapted for manufacturing at least an internal surface of said prosthesis, wherein said internal surface is designed for mounting onto a target site comprised in said dentition. The prosthesis typically comprises at least one coping and the aforesaid internal surface is an internal surface of said coping. At least one of the service center and the at least one said dental lab is adapted for designing an external surface of said coping based on said 3D numerical model.

Preferably, the service center comprises a material removal machine for directly manufacturing said coping from a suitable coping material based on the design of said internal surface and said external surface of said coping. Alternatively, the material removal machine may be used for manufacturing a physical model of said coping from a suitable wax material or the like based on the design of said internal surface and said external surface of said coping. The service center and/or at least one dental lab, and/or an external facility, comprises means for producing a negative cast of said physical model, and means for producing said coping from said negative model using a suitable coping material.

At least one said dental lab is adapted for manufacturing at least a second portion of said prosthesis based on said 3D numerical model. The dental lab is adapted for manufacturing at least an external surface of said prosthesis, wherein the external surface is designed for providing adequate clearance for the prosthesis relative to other teeth in said dentition adjacent to said prosthesis. Furthermore, the external surface is designed for providing adequate occlusion between the prosthesis relative to other teeth in said dentition opposite to said prosthesis.

The external portion of the prosthesis may be manufactured by a process involving adding at least one layer of material to a suitable coping and subjecting the layer to a material removal operation so that the surface of the layer conforms to a predetermined geometry. A plurality of layers may be sequentially formed over said coping, such that a final said layer conforms to the external surface required for the prosthesis.

Optionally, the fabrication of each layer, or of the layer (when the prosthesis only comprises a single layer), of the prosthesis may be performed using traditional methods. Such traditional methods are known in the art, and include, for example, building porcelain or any other suitable material layer by layer, starting with a first layer laid over the coping, and manually working these layers to fit within the space allowed for the prosthesis in the intra-oral cavity. To facilitate this, a physical (typically plaster or stone) model of at least a part of the intraoral cavity can be produced, typically by the service center and based on the 3D virtual model of the teeth, and this is sent to the dental lab.

Additionally or alternatively, the fabrication of said layer or layers is at least partially automated, and at least one dental lab comprises a material removal machine for removing material from said layer, and suitable scanning means for determining the topology of said layer prior to the material removing operation. Computer means are also provided for calculating machining paths for said material removal machine, wherein such paths are based on the difference between said topology of said layer prior to the material removing operation and the required topology for the surface.

The aforementioned predetermined parameters include a dimensional accuracy for the manufacture of a part of said prosthesis. In particular, when the dimensional accuracy for the manufacture of a particular part is required to be about 40 microns or less than 40 microns, for example the internal surface of the coping, the part is manufactured by said service center. Alternatively, when the dimensional accuracy for a particular part is required to be within substantially more than 40 microns, for example an external part of the crown, this part is manufactured by a dental lab.

In one particular application of the invention, a scan of the intraoral cavity is taken at a dental clinic, and the virtual model data thus obtained is sent to a dental lab. Then, the dental lab defines the margin line of the preparation (in the virtual model) and designs the coping geometry. Alternatively, the virtual model is (also) sent to the service center, together with a suitable prescription from the dental lab, in which case the service center defines the margin line of the preparation (in the virtual model) and designs the coping geometry. In either case, the coping geometry is processed by the service center, which then produces a coping based on the design, either directly, or indirectly via a lost wax process, for example. The coping, together with a physical positive model of the dentition, or a part thereof comprising the preparation, is sent to the dental lab, wherein the technician there prepares the full prosthesis in a traditional manner, by sequentially adding one or more layers of porcelain or other suitable material to the coping, and shaping the layers to produce the outer form of the prosthesis, checking with the physical model that the prosthesis will fit in the space left for it and provide adequate occlusion. The prosthesis is then sent to the dental clinic to be fitted to the patient.

Full flexibility in communication between the clinics, laboratories and the service center is provided, enabling for example, many different communications to be performed therebetween, including the following non-limiting illustrative examples:

(i) scanned data of the intraoral cavity (from which a virtual model thereof is generated) is sent from the dental clinic to the dental lab and/or service center;

(ii) 3D numerical data (i.e., the virtual model) of the intraoral cavity, created directly at the dental lab or service center, or indirectly from data transmitted to either location, is transmitted to the dental clinic for approval;

(iii) approved 3D numerical data of the intraoral cavity, wherever created, is transmitted to the dental lab and/or to the service center;

(iv) definition of the margin line by means of the dental lab or the service center is sent to the dental clinic for approval;

(v) approved margin line definition is sent to the service center and/or dental lab from the dental clinic;

(vi) definition of the 3D coping geometry by means of the dental lab or the service center is sent to the dental clinic for approval;

(vii) approved 3D coping geometry, and/or approval thereof, is sent to the service center and/or dental lab from the dental clinic;

(viii) prescription for the coping is sent from the dental lab to the dental clinic for approval, and approved prescription is sent to dental lab and/or service center.

Herein, "dental clinic" refers to the interface between a dental practitioner and a patient, and thus includes any physical entity, in particular a clinic, in which there is interaction between a dental patient and a dental practitioner. While "dental practitioner" typically refers to a dentist, doctor, prosthodontist or orthodontist, it also includes herein all other caregivers that may interact with a dental patient during the course of a dental treatment. While "dental patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, and any other artificial partial or complete denture.

The terms virtual model, 3D numerical model, and the like, are used interchangeably herein to refer to a computer simulation of a surface, comprising 3D topographic data referring to the surface, such a surface typically being dental surfaces of the intraoral cavity.

In another aspect of the invention a system and method are provided for designing and producing dental appliances, such as for example braces. The system comprises at least one dental clinic and at least one dental laboratory. The system also comprises a dental service center that is separate from the dental laboratory. The service center is equipped to generate a virtual 3D model of a patient's teeth from data obtained either by optically scanning the teeth directly or by scanning a physical model of the teeth, the process being at least initiated at the dental clinic. Alternatively, the dental lab may generate the virtual model. The service center is also equipped to use the computer model to design a dental treatment and to select or design and to manufacture appliances to carry out the treatment. The details of the treatment and of the required appliances may be then sent to the clinic. The clinic may then send instructions to a dental laboratory which is equipped to make at least a part of the dental appliances in accordance with instructions received from either a dental clinic or from the service center, and the appliances are then dispatched to the clinic.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
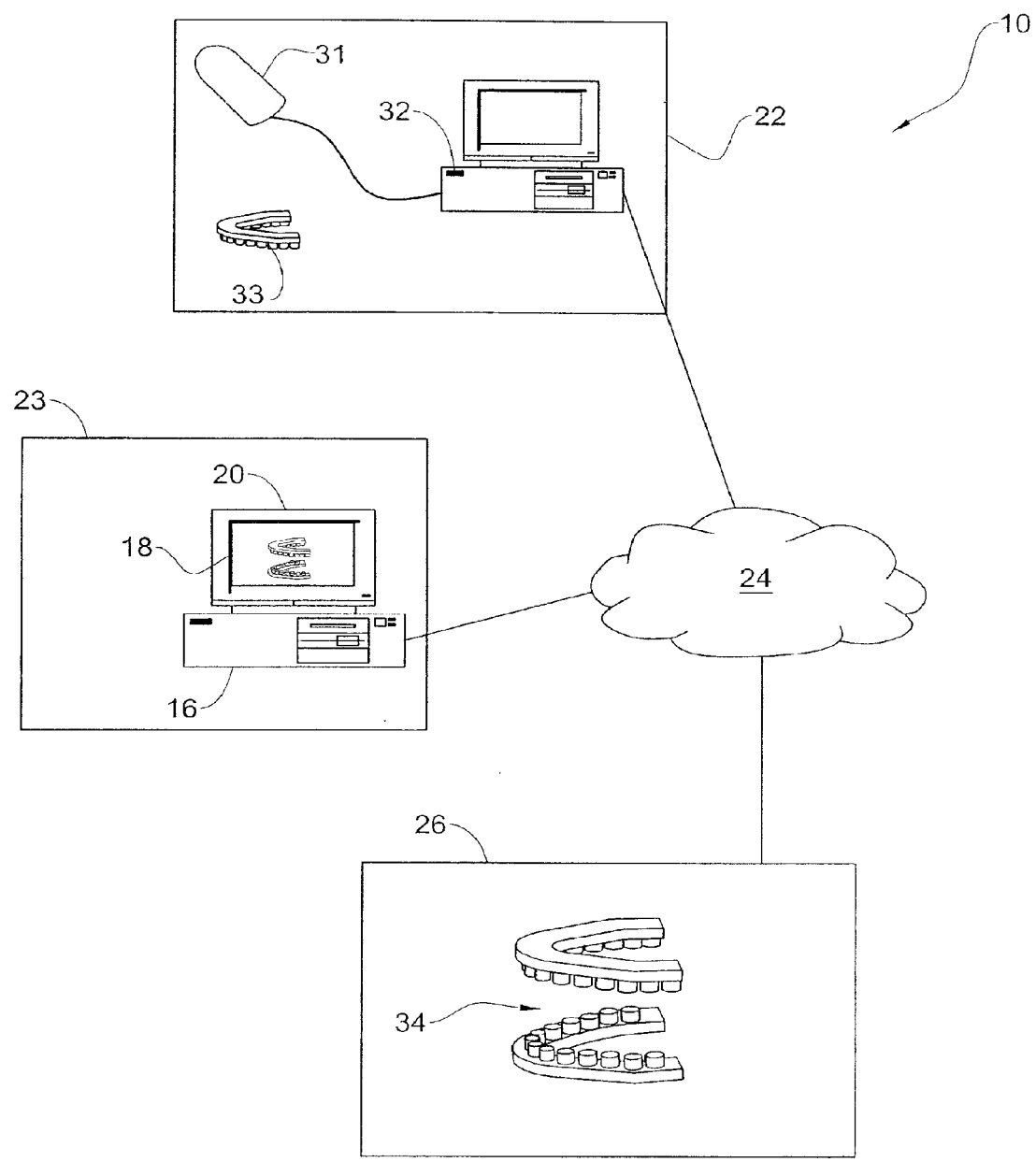
FIG. 1 shows a dental service system for designing and producing dental appliances in accordance with one embodiment of one aspect of the invention.

FIG. 1 illustrates a system 10 for designing and producing dental appliances, in accordance with the invention. The system 10 comprises a dental service center 23, one or more dental clinics 22, and one or more dental labs 26. The dental clinics 22 and the dental labs 26 are linked to each other and each to the dental service center 23 via a communication means or network such as for example the Internet or other suitable communications medium such as an intranet, local access network, public switched telephone network, cable network, satellite communication system, and the like, indicated by the cloud at 24. Optionally, it is also possible for some dental clinics 22 to be linked to each other, and/or for some dental labs 26 to be linked to each other, via the same one or a different one of said communication medium, for example when such dental clinics or labs form part of a common commercial entity. Further optionally, such interlinked dental clinics 22 and/or dental labs 26 may be further linked with other entities, for example a head clinic or head lab, comprising a centralized data base (not shown).

According to the invention, digitised three-dimensional (3D) information W (FIG. 2) of the patient's intra-oral cavity, or part thereof, is created by the system, and this information is then used by the dental labs 26 and/or the service center 23 for designing and/or manufacturing a custom dental prosthesis in an optimal and cost efficient manner. Accordingly, acquiring an accurate 3D representation of the intraoral cavity is the first step that is carried out by the system. Typically, the 3D information is obtained at the clinic 22, but this information may be obtained, alternatively, by one of the dental labs 26 or the service centre 23, as described herein.

Preferably, each dental clinic 22 may provide the 3D digitized data of the intraoral cavity, including the dentition and associated anatomical structures of a patient, and thus comprises suitable equipment for scanning a patient's teeth. Such equipment may include, for example, a hand-held scanner 31 that is used by the practitioner to acquire the 3D data. Advantageously, a probe for determining three dimensional structure by confocal focusing of an array of light beams may be used, for example as manufactured under the name of PROSTHOCAD or as disclosed in WO 00/08415, the contents of which are incorporated herein by reference in their entirety. The 3D data obtained by the probe may then be stored in a suitable storage medium, for example a memory in a computer workstation 32, before being sent over the communication network 24 to the dental service center 23 and/or to the dental lab 26, for further processing, as described below.

Alternatively, each clinic 22 may include equipment for obtaining a negative casting of a patient's teeth. In this case, the negative cast or impression is taken of the patient's teeth, in a manner known in the art, and this negative model 33 is dispatched to one of the dental labs 26 that is equipped to prepare from the negative model a positive cast 34 suitable for scanning. The positive cast 34 may be scanned at the dental lab 26 by any method known in the art, including using the aforesaid probe manufactured under the name of PROSTHOCAD or as disclosed in WO 00/08415. The 3D data is then transmitted over the network 24 to the service center 23. Alternatively, the positive cast 34 may be dispatched to the service center 23 by the dental clinic 22 and scanned at the service center to obtain the 3D data. Alternatively, the service center 23 produces a positive model 34 from the negative model 33 and is scanned thereat, or sent to the dental clinic 22 to be scanned thereat. Alternatively, the negative model 33 is scanned, either at the dental lab 26 or at the service center 23.

Alternatively, the negative model 33 provided by the clinic 22 is sent to the service center 23, either directly by the clinic 22, or indirectly via the dental lab 26, and a composite positive-negative model may be manufactured from the original negative model. Thereafter, the positive-negative model may be processed to obtain 3D digitized data, for example as disclosed in U.S. Pat. No. 6,099,314, assigned to the present assignee, and the contents of which are incorporated herein in their entirety.

Alternatively, the 3D digitized data may be obtained in any other suitable manner, including other suitable intra oral scanning techniques, based on optical methods, direct contact or any other means, applied directly to the patient's dentition. Alternatively, X-ray based, CT based, MRI based, or any other type of scanning of the patient or of a positive and/or negative model of the intra-oral cavity may be used. The dimensional data may be associated with a complete dentition, or of a partial dentition, for example such as a preparation only of the intra oral cavity.

Once the 3D digitized data is obtained, the next step is to design the dental prosthesis in question, followed by the manufacture thereof, and finally the installation of the appliance in the oral cavity of the patient.

The design and the manufacture of the appliance may each be carried out at the dental lab 26 or at the service centre 23, or alternatively one or both of these activities may be shared between the two; in each case the design and manufacture are based on the original 3D data of the oral cavity previously obtained.

The dental lab 26 comprises a laboratory, or a design or manufacturing entity that provides direct technical services to the dental clinic 22. Such services include, for example, scanning, manufacturing, analyzing the preparation in the intra oral cavity to mark the location of the finish line, for example, as disclosed in U.S. Ser. No. 10/623,707 and WO 04/008981, also assigned to the present assignee, and the contents of which are incorporated herein in their entirety, and so on. The dental lab is characterized as being equipped or otherwise able to design part or whole appliances, and/or to partially manufacture or assemble the same, particularly where close tolerances are relatively less critical. On the other hand, while the service center 23 is also equipped to design part or whole appliances, and/or to fully or partially manufacture and/or assemble the same, it is particularly suited to do any of these activities where close or tight tolerances are in fact critical and/or difficult to achieve.

The service centre 23 is a different design and manufacturing entity to the dental lab 26 and is thus separate thereto. However, while the service centre 23 may be located in a different geographical zone to the dental clinic 26, for example, different countries, different cities in the same country, different neighborhoods in the same city, or even different buildings in the same neighborhood, they may also be housed in the same building, and in any case maintain their separate functions and capabilities, as described herein.

Typically, for any given prosthesis, the service center 23 shares at least the manufacturing of the prosthesis with one dental lab 26 according to predetermined criteria, as will be further elaborated herein. Nevertheless, the manufacturing for a particular prosthesis may also be shared between the service center 23 and a number of dental labs 26, each of which contributes a part of the manufacture. The same applies also to the design of the prosthesis, which may be executed at the same or a different dental lab 26, and optionally also shared with the service center 23.

The dental lab 26 is typically located in the same locality as the clinic 22 that it services, though the two may alternatively be geographically remote. Thus, the dental lab 26 and the clinic 22 that it services may both be located in the same building or complex, or in different parts of the same city, or in different cities or countries. However, the dental lab 26 of the invention typically has an established working relationship with the clinic 22, and thus tends to be, generally, within the same city.

Figure 2:
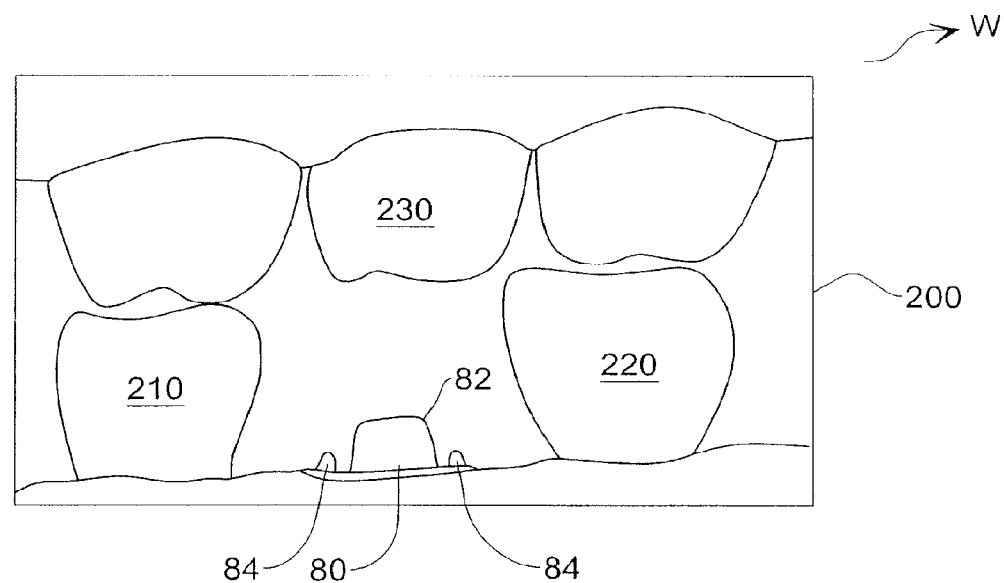
FIG. 2 illustrates a portion of the intra oral cavity of a patient wherein it is desired to implant a prosthesis.
Figure 3:
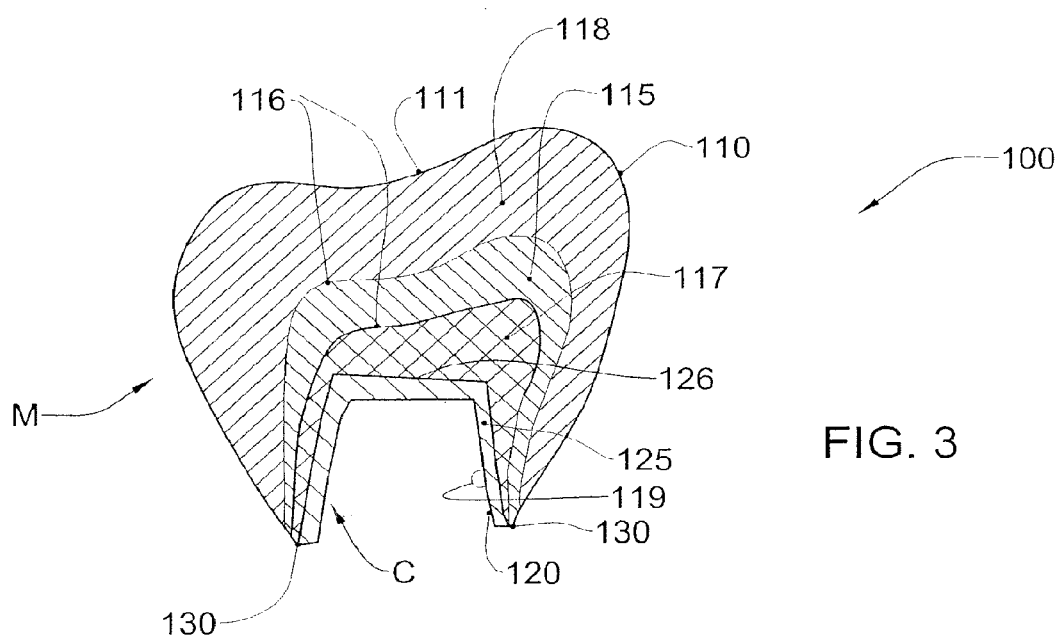
FIG. 3 illustrates in cross sectional view a crown prosthesis having a coping and a multiple layered cap.

In a first embodiment of the present invention, the dental appliance to be manufactured is a prosthesis such as a crown. Referring to FIGS. 2 and 3, such a crown, generally designated 100, has an internal surface 120 and lower edge 130 that needs to be very precisely defined and manufactured to match the preparation 80 and finish line 84, respectively, in the intraoral cavity 200 of a patient. Such a crown typically comprises a cap 110 and a coping 125.

Referring to FIG. 1, the communication network 24 may also used to send a prescription from a clinic 22 and/or dental lab 26 to the service center 23, and/or between the clinic 22 and the dental lab 26, for example when the dental practitioner in the clinic 22 interacts with the dental lab 26 to finalize the prescription for the service center 23. The prescription may include instructions from a dentist at a clinic 22 and/or from the dental lab 26 specifying which of the patient's teeth is to be restored, the material to be used for the restoration (for example, the form and material of the shoulder, whether metal or ceramic shoulders are to be provided in the lingual and buccal parts of the prosthesis, and so on), the color of the required restoration, comments about the margin line (finish line), and so on.

While the term "preparation" refers to the stump left of the tooth that is to be replaced by the crown and on which the crown is to be mounted, it also includes artificial stumps or other devices that may be implanted in the intraoral cavity in such a position or in a position that is optimal for implanting the crown.

The cap 110, which may be formed from a plurality of layers 115, preferably needs to have a natural looking appearance, and thus the color and surface features of the cap 110 need to be matched to those of the other teeth of the intra oral cavity 20, particularly those in proximity to the site in which the crown 100 is to be implanted. Further, the dimensions of the cap have to be such as to enable the crown to fit between the adjacent teeth 210, 220, and to provide proper occlusion with the teeth 230 of the facing jaw. The manufacturing tolerances for the cap 110 are not as tight as for the inner surface 120, and may be of the order of about 80 microns, which is within the capabilities of most regular dental labs 26 that currently provide such services to clinics 22.

The coping 125 is made from a metal, ceramic, or other very strong material, and is designed for taking the mechanical loads of the crown 100 associated with the normal activity of the teeth. The coping 125 serves as a preparation coupling portion of the prosthesis. The inner surface 120 and lower edge 130 of the coping 125 need to closely match the preparation 80 and finish line 84, and moreover provide a reasonable insertion path for the crown 100. Typically, the fitting tolerance for the internal surface 120 and lower edge 130 needs to be in the order of about 40 microns or less, which is more demanding than for the cap 110. If the dimensional accuracy is not maintained to this tolerance level, there is a risk of infection of the remaining parts of the tooth, the infection entering via the gap between the crown and the preparation, in particular between the lower edge 130 and the finish line 84. Furthermore, where such tolerances are not met, the life of the prosthesis may be severely reduced. Although prior art dental labs do design and manufacture copings, such close tolerances are not typically achievable by most regular dental labs that currently provide such services to clinics. Accordingly, the design and manufacture of the internal surface 120 and lower edge 130 may be advantageously carried out according to the present invention by the service centre 23, which has the equipment and expertise to do so. By centralizing such specialized and accurate work from a number of clinics 22, the service center 23 is able to carry out such work in a more cost effective and efficient manner, and generally more accurately, than the dental lab 26.

Figure 4:
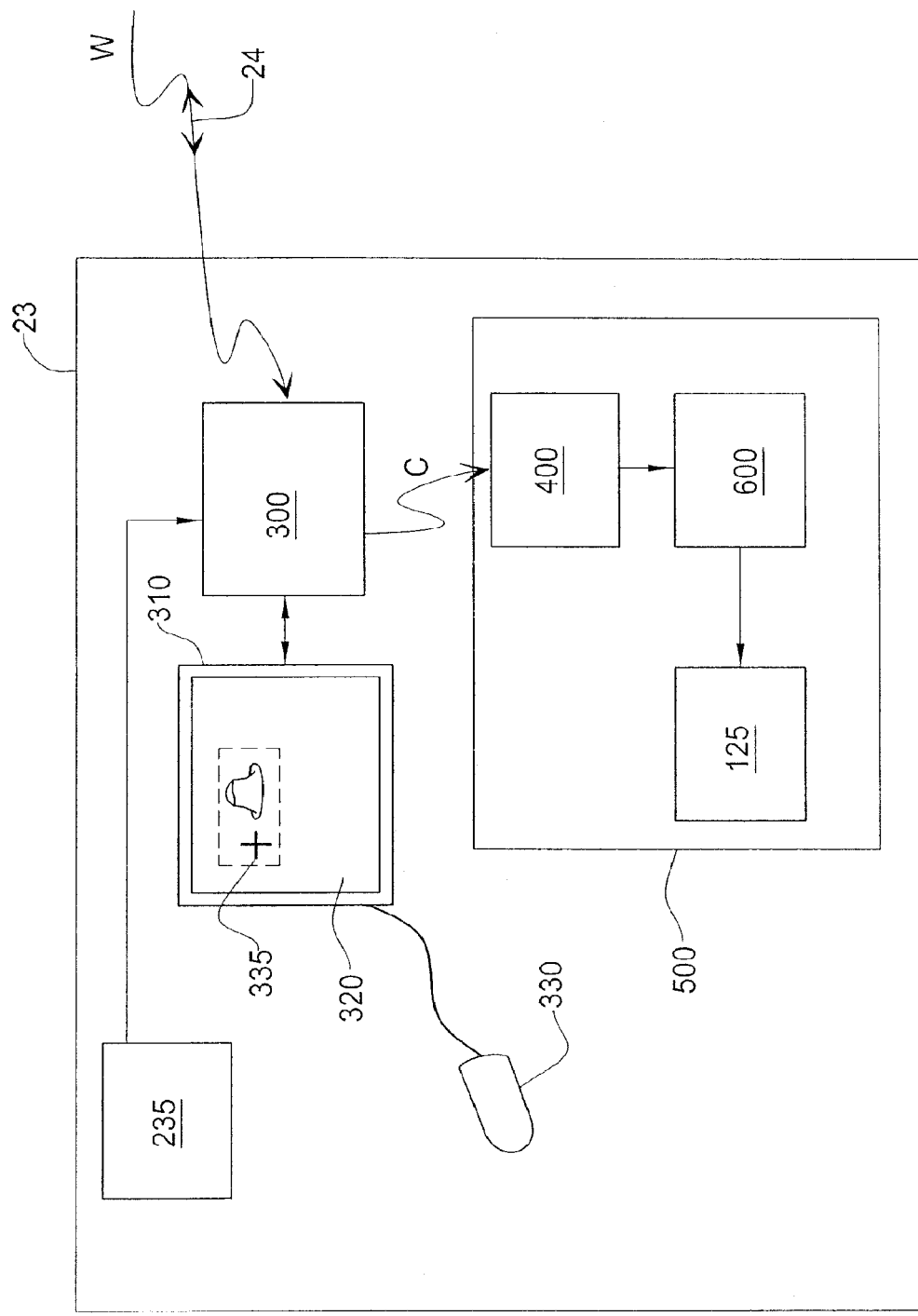
FIG. 4 illustrates a service center according to the first embodiment of the invention.

Referring to FIG. 4 in particular, the service centre 23 comprises suitable hardware such as a server 300 that is suitably programmed to receive the 3D data W of the oral cavity 200, as well as the prescription from the clinic 22 or from the dental lab 26, or possibly the data and the prescription may be provided from a different one of said clinic 22 or dental lab 26. Alternatively, the data W is provided by the server 300 or another computer at the service center 23 which is adapted for providing 3D data from a negative-positive model of the cavity, or by any other means, as described above. The server 300 comprises suitable software to enable the 3D data corresponding to the external surface 82 of the preparation and finish line 84 to be isolated from the rest of the 3D data W of the oral cavity 200, and this may be done in an automated manner. Alternatively, this selection of the data may be done interactively by specialized personnel. Thus, the server 300 optionally comprises at least one monitor or other display means 310 for displaying the 3D data as a manipulable image 320, whereby by means of a mouse 330, keyboard, voice recognition means, or any other suitable user interface the said personnel may choose demarcation points on the image, which in his/her opinion correspond to the finish line. These points may be marked with the help of a cursor 335 or other icon or the like on the display means 310. The server 300 also has suitable software to define the inner surface 120 according to predetermined parameters. These parameters take into account the geometries of the external surface 82 of the preparation 80 and finish line 84, the spacing required between the coping and the preparation to accommodate the adhesive or cement that is used to provide the bond between the two, and also the insertion path geometry, which is a function of the topology of preparation 80 as well as of the adjacent teeth 210, 220. The server 300 also comprises suitable software to automatically or interactively provide the external shape of the coping 135, and thus provide a complete geometrical representation or 3D data C of the coping, digitally. The external surface 126 of the coping 125 may be defined in any number of ways. Typically, at least a majority of the external surface 126 is displaced from the internal surface 120 by a uniform amount to provide an approximately constant thickness throughout. However, the thickness of the coping may vary for a number of reasons. For example, it may be necessary in some cases to provide a coping that is stronger in some parts than in others, reflecting the activity that the crown 100 will be expected to engage in—as a molar, incisor, canine and so on. Also, the preparation may be of such a shape that in some areas relatively little room is left for the coping 125, while in other areas there is a wider gap between the coping and the next tooth. The wider this gap is, the thicker the coping may be, while still permitting sufficient material for the cap 110 to be provided. In cases where the cap 110 is cemented or bonded onto the coping using an adhesive, it may be desired to provide more adhesive between the lower edge of the coping and the cap relative to other parts between the coping and the cap. Accordingly, the outer surface 126 may be somewhat recessed close to the lower edge 130, and thus the coping may be thinner here. The additional adhesive that may be provided at the recess relieves some mechanical stress from the lower edge of the cap 110, which is structurally the weakest part thereof, typically, thus prolonging the life of the crown 100.

The server 300 is further adapted to provide machining instructions to a suitable material removal machine 400, based on the geometrical 3D data C of the coping 125. Alternatively, the server 300 transmits the 3D data C to another computer (not shown) that provides the machining instructions to machine 400. The service center 23 further comprises a suitable manufacturing centre 500 for manufacturing a solid replica corresponding to the 3D data C. Optionally, the manufacturing center 500 comprises said machine 400, which may be adapted for producing a coping 125 directly from a suitable hard material, using the machining instructions. Any suitable machining tool may be used that is adapted for material removal, and may include inter alia mechanical tools such as drills for example, laser tools such as for example laser drills or cutters, ultrasonic tools such as for example ultrasonic cutters, and so on. The machining paths and material removal characteristics of such tools can be finely controlled, typically by a control computer comprised in or operatively connected to said machine 400. Thus, the coping may be manufactured directly from the crown material, such as a metal for example, by means of machine 400.

Preferably, the coping is manufactured indirectly, in a manner such as described for example in U.S. Ser. No. 60/459,624 or WO 2004/087000, also assigned to the present assignee, and the contents of which are incorporated herein in their entirety by reference. Essentially, a physical model of the coping is machined from a suitable wax or similar material, by a material removal process using a suitable machining tool and the machine 400, wherein the machining is computer controlled and based on the 3D data C. Then, the wax model is transferred to a casting facility 600, comprised in the manufacturing centre 500, or alternatively provided by a source external to the service center 23, including for example the dental lab 26, and a negative mold of the wax model is produced, typically by a lost-wax process. Thereafter, the mold is used for forming the coping 125, either by flowing a molten metal into the mold and allowing solidification of the metal, or by injecting ceramic powder thereinto and heating the same until the ceramic powder sinters and forms a solid integral unit, or by another suitable method. The mold may then be removed, thereby providing a coping 125 that is dimensionally faithful to the 3D data C to high dimensional accuracy, typically within 40 microns or less.

The wax-based method for producing the coping 125 has some advantages over the direct material removal method, for example less wear and breakage is experienced by the machining tool, and thus lowers costs. Furthermore, deformations of the tool, when a direct contact tool such as for example a mechanical tool is used, is less likely, and thus less deviations from the nominal dimensions (i.e. 3D data C) of the coping 125 occur than when producing a coping directly from a metal or other hard material.

Once the coping 125 has been manufactured, the cap 110 can be bonded thereto, if manufactured separately. Alternatively, and typically, the cap 110 is manufactured already joined to the coping, as will become clearer herein. In either case, the external surface 111 of the cap 110 needs to be defined first. The external surface 111 is such as to provide:

(a) adequate clearance between the crown 100 and adjacent teeth 210, 220 when the crown is fixed onto the corresponding preparation in the intraoral cavity 20; and (b) adequate occlusion between the crown 100 and the teeth 230 of the opposite jaw when the crown 100 is fixed onto the corresponding preparation in the intraoral cavity 20.

At the very least, the external surface 111 of the cap 110 is such as to provide certain critical linear dimensions that comply with at least one of the target width or target height of a site or location on the jaw on which the crown is to be fitted. The target width may include the mesiodistal size of a tooth that is being replaced by the crown, and may be defined such as to provide adequate clearance between the crown and adjacent teeth when the crown is fixed onto the corresponding preparation in the intraoral cavity. The target height may be defined such as to provide adequate occlusion with the "working side" of the tooth and avoiding interfering contact between the crown and teeth of the opposite jaw when the crown is fixed onto the corresponding preparation in the intraoral cavity.

An outer shape for the external surface 111 may be chosen, and this can be accomplished in a number of ways. For example, if the original tooth that the crown 100 is replacing is still available, and the outer surface thereof is of a reasonable form, the tooth may be scanned and the 3D data of the surface obtained. If necessary, this 3D data may be considered as a starting point, and the final shape of the external surface 111 is obtained by manipulating this data as required by the technician or other user that is designing the surface 111. Alternatively, if the patient has a reasonably healthy tooth on the same jaw but on the adjacent quadrant at a position corresponding to where the crown 110 is to be fitted, the 3D data of the surface of this tooth is obtained. Optionally, this tooth may be scanned as described herein to obtain the 3D spatial coordinates thereof, unless this data may already be available from the 3D data of the oral cavity 200 stored in the server 300. Alternatively, a suitable profile for surface 111 may be chosen and obtained from a library 235 that comprises the 3D spatial profiles of shapes or profiles of the outer surfaces of a plurality of crowns and teeth. If necessary the relative size and shape of the surface 111 may be adjusted by the technician to better match the other teeth in the jaw. Then, the chosen surface is adjusted in any suitable manner, either manually, automatically, interactively or in any other manner, in order that the required target dimensions of surface 111 will fit within a control volume that defines the maximum dimensions of the cap, as required to conform to the space available in the intra oral cavity 200. In particular, the control volume is chosen such as to provide adequate clearance between the crown and adjacent teeth, and adequate occlusion with the opposite teeth, when the crown is properly fixed onto the preparation.

Figure 5:
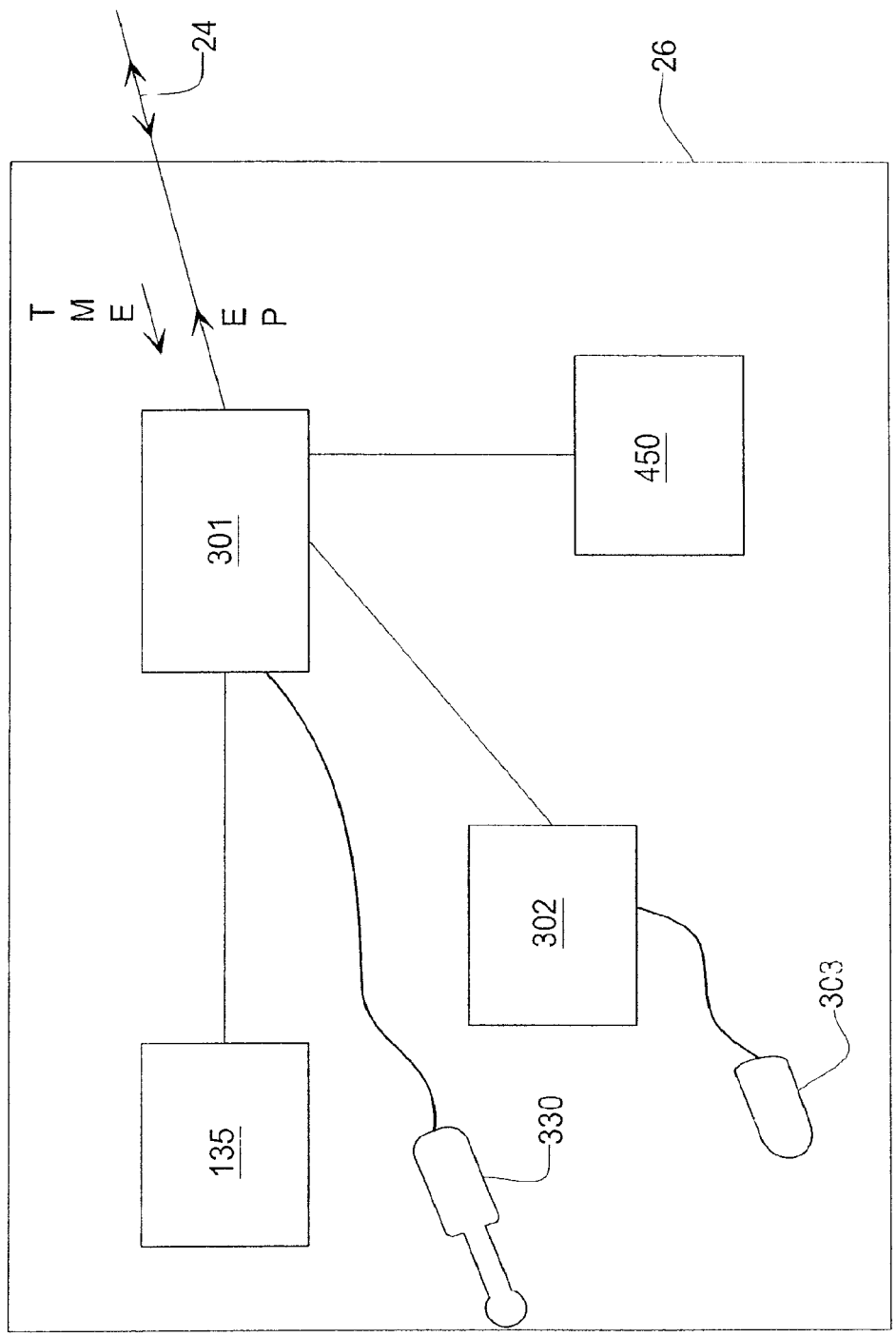
FIG. 5 illustrates a dental lab according to the first embodiment of the invention.

The design of the external surface 111 may be executed at the service center 23 or at the dental lab 26. If at the latter, and if use is made of a library of 3D spatial profiles of shapes or profiles of the outer surfaces of a plurality of crowns and teeth, then the dental lab 26 can make use of library 235 of the service centre 23, via communications network 24. Alternatively, the dental lab 26 may have its own digital library 135 of 3D spatial profiles of shapes or profiles of the outer surfaces of a plurality of crowns and teeth, operatively connected to a local server 301 or other computer, as illustrated in FIG. 5, which comprises a suitable display 302 and user interface 303 such as a mouse and/or keyboard. The local server 301 is in any case in communication with the server 300 of the service center 23 and a computer 32 of the dental clinic 22 via network 24.

Optionally, and according to predetermined criteria, the details, including shape and size of each of the intermediate layers 115 can also be chosen or determined, such as are considered that will provide a particular or desired visual effect, for example. Thus, it may be decided, for example, to provide an outer layer made from an opalescent porcelain, but having a varying thickness, so that at some zones an intermediate layer will appear more reflective than at others. Similarly, an intermediate layer can be made from a suitable porcelain having a desired color, and the depth of this layer can also be varied to provide different hues of the color. For example, at places where the depth of the layer 115 is greater, the layer 115 will appear a little lighter than where the layer is shallower. This aspect of the design of the cap may be executed by the service center 23 or by the dental lab 26.

Once the design of the cap 110 is complete, the next stage, that of manufacturing the cap 110 can begin. As mentioned before, there are at least two methods for manufacturing the cap 110—as a separate item which is then bonded to the coping 125; or together with the coping 125.

In the first method, the inner surface of the cap 110 needs to be defined, and the design takes into account a number of parameters, such as for example the geometry of the external surface 126 of the coping 125, the spacing required between the cap 110 and the coping 125 to accommodate the adhesive or cement that is used to provide the bond between the two. It should be noted that if this method is adopted, it is preferable for the shape of the external surface 126 of the coping to be designed such as to provide an adequate insertion path geometry for the cap 110, which is a function of the external surface 126 as well as of the adjacent teeth 210, 220. Thus, if necessary, a damaged cap may be replaced on a coping 125 that is already cemented on the preparation 80, without having to remove the coping 125 from the preparation 80 and thus avoid possibly damaging the same. Since the 3D data of the cap 110, internally and externally is known, it is possible to manufacture a replacement cap 110 without having to rescan the oral cavity. Alternatively if the whole crown 100 were to be replaced, the preparation area would need to be rescanned, as the geometry thereof may have changed as a result of removing the coping 125.

The next step is to combine the 3D data of the internal surface of the cap 110 and 3D data of the external surface 111 of the cap 110, to provide a complete 3D digital model M of the cap. The 3D model M may be designed at the dental lab 26 or at the service center 26 itself, using the original 3D information W of the intraoral cavity 20, and particularly the 3D model of the coping 125 that was previously created. Where this activity is executed at the dental lab 26, the corresponding design software in server 300 is accessed by the technician at the lab 26 via the communications network 24. Alternatively, the design software may be comprised in the computer 301 at the dental lab 26, and the required data, including the 3D data C of the coping 110, may be acquired from the service center 23 via the communications network 24. The 3D model M is then converted, preferably by server 300 or alternatively by computer 301, into machining instructions E for machine 400, for example. Thereafter, the cap 110 may be manufactured in any one of a number of ways.

For example, the said machine 400, may be adapted for producing the cap 110 directly from a suitable durable material, using the machining instructions based on model M. As for the coping 125, any suitable machining tool may be used that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by a control computer operatively connected to or comprised in machine 400.

Alternatively, the cap 110 may be manufactured indirectly, using a wax-loss process similar to that described herein and in U.S. Ser. No. 60/459,624, for the coping, mutatis mutandis. Thus, a physical model of the cap is machined from a suitable wax or similar material, by a material removal process using a suitable machining tool and the machine 400. Then, the wax model is transferred to a casting facility, which may be the same or a different casting facility 600, comprised in the manufacturing centre 500, or alternatively provided by a source external to the service center 23, including for example the dental lab 26, and a negative mold of the wax model is produced, typically by a lost wax process. Thereafter, this mold is used for forming the cap 110, either by flowing a molten metal into the mold and allowing solidification of the metal, or by injecting ceramic powder thereinto and heating the same until the ceramic powder sinters and forms a solid integral unit, or by any other suitable means. The mold may then be removed, thereby providing a cap 110 that is dimensionally faithful to the 3D model M to high dimensional accuracy, typically within about 40 microns or less.

If it is required to manufacture the cap 110 from a plurality of different layers of materials, for example to provide a natural looking appearance that matches the other teeth of the patient, this may be done as follows. First, the 3D model M may used to design the outer shape of the outer surface 116 of each intermediate layer, as illustrated in FIG. 3. The 3D models T, each corresponding to one intermediate layer 115, and of course including the final layer 118 are converted, typically by server 300 or alternatively by computer 301, to material removal instructions P which are executable by a suitable material removal machine such as for example machine 400. Then, the innermost layer 117, i.e., the layer that is to be mounted directly to the coping 110, is manufactured by direct material removal methods or by indirect methods such as a lost-wax process, similar to that described above for the whole cap 110, mutatis mutandis. This stage of the manufacture, since it requires high dimensional accuracy, is preferably carried out at the service center 23. Where an indirect method is used, at least the wax model is manufactured at the service center 23 for the same reason. Then, successive layers 115 of material up to a final layer 118 may be added to the inner layer 117, in a manner known in the art, and each layer is subjected to a material removal operation so that the external surface 116 thereof matches the design geometry, i.e., 3D data T. The dimensional accuracy of the surfaces 116 can be 80 microns or less, and that of external surface 111 of the cap 110, i.e., of the final layer 118, is preferably about 80 microns, and thus, the material removal operations for the intermediate and final layers may be advantageously carried out at the dental lab 26.

In the second method, the cap 110 is produced already joined with the coping 125, i.e. starting with a workpiece comprising the coping 125. Essentially, a layer of suitable crown material is added to the coping 125 in a manner known in the art, and this layer is then subjected to a material removal operation to provide the desired profile for the external surface 111, for example in a manual fashion, as is well know in the art, or alternatively in a computer controlled manner, for example similar to that as described above for the separate cap, mutatis mutandis.

Thus, there is no need in this embodiment to define an inner surface for the cap 110, since material is applied directly to the coping 125, automatically assuming the appropriate shape over the coping's outer surface, and therefore high dimensional accuracy between the cap 110 and coping 125 is automatically achieved.

Where it is desired to manufacture the crown in which the cap 110 comprises a plurality of layers 115 including a final layer 118, for each layer suitable crown material may be added to the previous finished layer and subsequently machined or otherwise subjected to a material removal operation, manually or computer-aided, to provide the required profile for each external surface 116 of the layers, including the outer surface 111 of the cap 110.

When the crown is fabricated in the traditional fashion at the dental lab 26, including one or more material layers built up over the coping manufactured by the service center 23, there is less need for the outer surfaces of each layer to be precisely defined in a virtual model. Thus in such cases the technician at the dental lab 26 may design the cap 110 in any suitable manner, including traditional methods or any other method, including manual, interactive of automated methods, or a combination of two or more thereof.

For the first and second methods described above, the material removal operations for the innermost layer 117, intermediate layers 115 and final layer 118 can be performed at the dental lab 26, which comprises a suitable material removal machine 450 comprising any suitable machining tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by a control computer operatively connected to or comprised in machine 450 in which the machining instructions P, previously prepared, are stored. Alternatively, the material removal operations are carried out in the dental lab 26 using more traditional methods. Particularly for this purpose, a physical positive model of the teeth, particularly including the preparation and surrounding teeth including the adjacent teeth and the facing teeth of the opposite jaw, is provided to the dental lab 26, which assists the technician in fabricating the full prosthesis. Such a physical model can be made from the virtual model W using any suitable method, such as for example material removal methods including CNC machining methods, or using other techniques, for example prototyping methods, typically at the service center 23, though optionally at the dental lab 26. Alternatively, and particularly if a negative model was used to obtain the virtual model in the first place, the positive model may be produced directly from the negative model in a manner known in the art.

It should be noted that when the manufacture of the external surfaces 116 of the layers 117, 115 and 118 of the coping 110 is conducted in a different machine to that used for the manufacture of the internal surface of the cap 110 (in the case of the first method) or of the coping 125 (in case of the second method), proper spatial alignment between the internal surface and the external surfaces of each component must be maintained. This may be achieved in a number of ways. For example, surface features such as projections 119 of a known geometry and located at a known position in inner surface 120 (or elsewhere) are included in the 3 model M, and thus also included in the physical coping 125 that is manufactured. The projections 119 are used as reference datums when the coping is moved to a different machine such as machine 450 to continue with the manufacture of the crown. When the cap 110 is manufactured separately from the coping 125, similar projections may be included in the cap 110, also serving as a reference datum for aligning the cap 110 with respect to the coping 125. Alternatively, once the coping 125 and mounted in the next machine, such as machine 450, the outer surface thereof is scanned by means of a suitable scanner, for example scanner 330, and the 3D data thus obtained is used by computer 301 to adjust the material removal instructions P such as to align the outer surface of the cap 110 with the coping 125.

Preferably, the material removal operations, for either the first or second methods, is carried out according to the method disclosed in U.S. Ser. No. 60/542,327, entitled "METHOD AND SYSTEM FOR MANUFACTURING A DENTAL PROSTHESIS", filed on 9 Feb. 2004, also assigned to the present assignee, and the contents of which are incorporated herein by reference thereto. Essentially, the crown 100 may be manufactured by performing a mapping operation to determine the three-dimensional shape of the outer surface of the material that is to be machined to form the crown 100, either the final layer 118 or any intermediate layer 115, including the inner layer 117, and then subjecting the layer to a material removing operation, wherein the machining paths are computer controlled on the basis of the local differences between actual and required shape, and optimized to reduce machining times. Alternatively, the crown 100 is manufactured by performing a measuring operation to determine at least some critical dimensions of the outer surface 111 of the prosthesis, either the final layer or any intermediate layer. These measurements are then compared to the corresponding nominal dimensions in which the crown is to be fitted, and then subjecting the layer to a material removing operation, wherein the machining paths are computer controlled and optimized to reduce machining times.

Accordingly, the distance between adjacent machining paths may be maintained, for example in the order of 0.02-0.2 mm, and an optimal amount of material can be removed in each sweep without damaging the prosthesis and/or the tool. There is therefore no need to arrange machining paths within a fictitious envelope, as these paths are designed to match the actual external details of the workpiece, i.e. the material layer before machining commences. Thus:

potential damage to the crown and/or tool by attempting to remove too much material in one sweep, as may happen if the material exceeds the limits of the envelope, is generally avoided; and, machining time is not wasted by passing the tool across empty air for some portion of the machining paths, as may happen if the material is well below the limits of the envelope.

According to this manufacturing process, then, for each layer that is added to the coping 125 (for the said second method) or to the innermost layer 117 (for the said first method, and thus also including the innermost layer 117 itself):

a) actual dimensional data for at least one parameter associated with said layer is obtained;

b) for at least one such parameter, a comparison is made between the actual dimensional data and predetermined target dimensional data that it is desired to conform said parameter to; and c) the layer is then subjected to a material removal operation by suitable machining means along machining paths which are a function of said comparison, such that after said operation the parameter associated with the layer substantially conforms with said target dimensional data.

The parameter is preferably a geometric parameter comprising surface coordinates of each layer, while the target dimensional data comprises the numerical values of the surface coordinates of an idealized or required outer surface of the prosthesis. The surface coordinates of said required outer surface are provided by the 3D models T.

The aforesaid actual dimensional data may comprise the actual surface coordinates of each layer prior to the material removal operation. In step (a) the layer is scanned with a suitable three-dimensional surface probe 330, typically comprised and used in said dental lab 26, and operatively connected to the computer 301. Such a probe preferably provides a three dimensional structure based on confocal imaging. Alternatively, the actual dimensional data may be obtained using any suitable intra oral scanning technique, based on optical methods, direct contact or any other means, applied directly to the patient's dentition. Alternatively, the data may be obtained using techniques based on scanning a positive and/or negative model of the intra oral cavity. Alternatively, X-ray based, CT based, MRI based, or any other type of scanning of the patient or of a positive and/or negative model of the intra-oral cavity. The dimensional data may be associated with a complete dentition, or of a partial dentition, for example such as the preparation only, and corresponds to 3D data W.

Alternatively, the aforesaid parameter is a geometric parameter comprising at least one linear dimension of said layer. The target dimensional data thus comprises the numerical values of at least one of the target width or target height of a location on the jaw on which the crown is to be fitted. The target width may include the mesiodistal size of a tooth that is being replaced for example, and may be defined such as to provide adequate clearance between the crown and adjacent teeth when the prosthesis is fixed onto the corresponding preparation in the intraoral cavity. The target height may be defined such as to provide adequate occlusion between said prosthesis and teeth of the opposite jaw when the prosthesis is fixed onto the corresponding preparation in the intraoral cavity.

Figure 6:
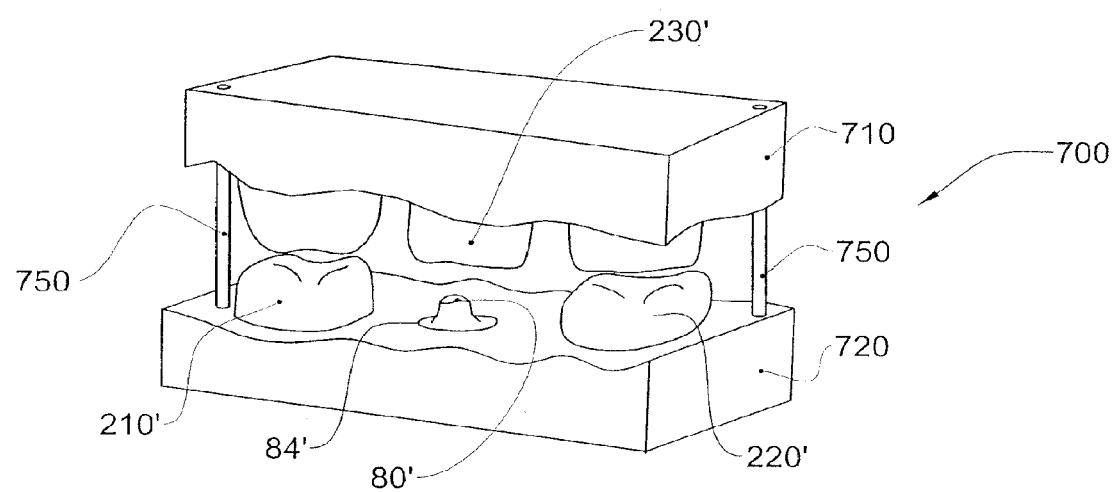
FIG. 6 illustrates a physical model of the intra-oral cavity of FIG. 2.

Referring to FIG. 6, the dental clinic 26 may also be provided with a physical model 700 of the part of the intra oral cavity of interest, namely comprising scale replicas the adjacent teeth 210, 220, preparation 80 and finish line 84, and upper teeth 230 opposite the preparation and the adjacent teeth, shown as 210', 220', 80', 84' and 230' in this figure. The model 700 is in two parts, an upper part 710 and a lower part 720 corresponding to the upper jaw and lower jaw, respectively and joined together reversibly in the correct occlusal relationship by means of alignment pins 750. The model 700 is preferably manufactured by the service centre 23 by any suitable means, for example via CNC machining of two solid blocks of a plaster or other material. The 3D data W that was originally taken from the intra oral cavity 20 is used for providing material removal instructions to machine 400, which can then manufacture the model 700 therefrom. The model 700 is then shipped to the dental lab 23, and helps the technician there to undertake fitting tests of the crown 100 with respect to the preparation 80' and finish line 84' in the model, before the finished crown 100 is finally sent from the dental lab 26 to the clinic 22 for implantation into the intra oral cavity 20 of the patient. Alternatively, particularly when the crown is built up on the coping using traditional methods, the model 700 may be used by the technician for designing and fabricating each of the successive layers of the cap, or when consisting of single layer, the design and fabrication thereof.

Figure 7:
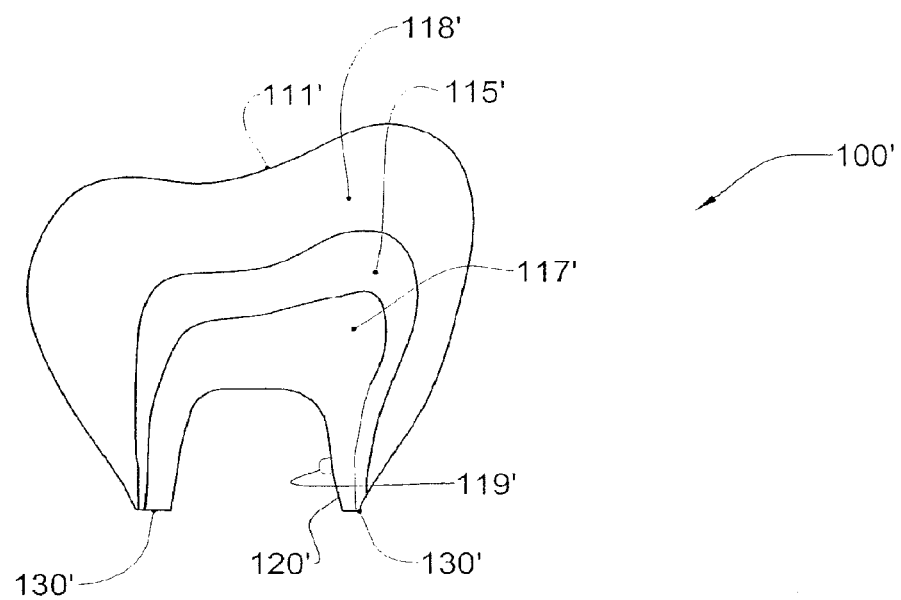
FIG. 7 illustrates in cross sectional view a crown prosthesis having a multiple layered construction.

Alternatively, the crown may be manufactured as a monolithic item, wherein the coping as such is not included as a separate item. Thus, referring to FIG. 7, the internal surface of such a crown 100' is required to fit over the preparation 80, and is thus designed and manufactured in a similar manner to the internal surface 120 of the coping 125 as described herein, mutatis mutandis, using direct material removal methods or indirect methods. Similarly, the external surface 111' is designed in a similar manner to external surface 111 of the cap 110, as described herein mutatis mutandis. The manufacture of the external surface 111' may be carried out at the service center 23, optionally concurrently with the manufacture of the internal surface 120' and lower edge 130'. However, it is also possible to send the unfinished crown 100', after the internal surface 120' and lower edge 130' thereof have been prepared by the service centre 23, to a dental lab 26, for a technician thereat to complete the manufacture of the external surface 111', in a similar manner as described herein for external surface 111, mutatis mutandis. The crown 100' may be made from number of layers, 118', 115', 117' and these may each be designed and manufactured in a similar manner to that described for crown 100, mutatis mutandis. However, it is important for the proper spatial relationship between the internal surface 120 and the external surface 111' to be maintained. For this purpose, the crown 100' may be mounted onto an alignment jig before the internal surface material removal operations begin. When the unfinished crown is shipped to the dental lab 26 it is transferred together with the jig, which maintains a known alignment with the manufacturing center 600 of the dental lab 26. Alternatively, the alignment may be achieved in other ways. For example, surface features such as projections 119' of a known geometry and located at a known position in inner surface 120' (or elsewhere) are included. The projections 119' are used as reference datums when the coping is moved to a different machine such as machine 450 to continue with the manufacture of the crown 100'. Optionally, such an alignment jig may comprise said model 700 of part or all of the dentition. Alternatively, once the crown 100' is mounted in the next machine, such as machine 450, the inner surface thereof is scanned by means of a suitable scanner, for example scanner 330, and the 3D data thus obtained is used by computer 301 to adjust the material removal instructions such as to align the inner surface of the crown 100' with the outer surface thereof.

Figure 8:
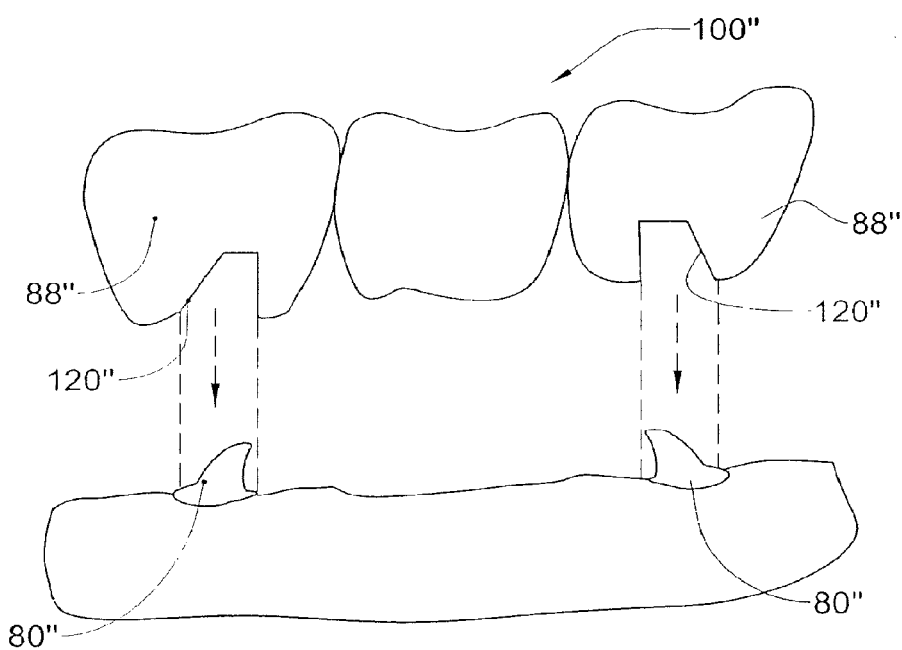
FIG. 8 illustrates the insertion path of a bridge prosthesis according to the invention.

While the design and manufacture of a crown prosthesis has been described, similar methods may be employed mutatis mutandis to design and manufacture any other dental prosthesis, including bridges, for example, and inlays, such as caps, for example, and any other artificial partial or complete denture. However, and referring to FIG. 8, when designing a bridge 100", care must be taken that the internal contact surfaces 120" for the abutment teeth 88" each provide an adequate insertion path 87" with respect to the preparations 80", taking into consideration the bridge 100" as a whole, and thus that the two paths 87" must be substantially parallel.

While the design and manufacture of a prosthesis has been described, based on a representation of surface information, the three dimensional entities in the oral cavity, such as for example the teeth gums and so on, and also the 3D entities that are designed by the system 10, including the coping 125 and cap 110, for example, may be described instead by solid representations.

In a second embodiment of the invention, the system 10 is used for orthodontical applications. The 3D data corresponding to the patient's intra oral cavity 20 is determined as for the first embodiment, mutatis mutandis. Referring to FIG. 1, the communication network 24 may also used to send a prescription from a clinic 22 to the service center 23. The prescription may include instructions from a dentist at a clinic 22 specifying which of the patient's teeth are to be moved in a dental treatment, as well as the desired final teeth positions at to be attained at the conclusion of the dental treatment.

The service center 23 executes a dental treatment planning software program at a computer station 16 having a central processing unit, such as a personal computer. The software imports the 3D digital data indicative of the patient's teeth previously obtained, and possibly a prescription sent from one of the dental clinics 22. The software processes the 3D data to generate a 3D computer model 18 of the dentition that is displayed to a user on a monitor 20. The treatment planning software includes features to enable the user to manipulate the model 18 to select or design dental appliances for the patient to execute the treatment specified in a prescription sent from the clinic. For example, the user can select or custom design one or more dental appliances (e.g. brackets or archwires) and apply virtual models of these appliances to the 3D model of the teeth. In the case of orthodontic appliances, the software may be configured to move the virtual teeth in accordance with predetermined rules based upon the applied appliances in order to simulate the movement of the teeth that would occur in an orthodontic treatment in which the appliances are applied to the patient's actual teeth. The user then determines whether the selected dental or orthodontic appliances are satisfactory. If not, the user selects new appliances and repeats the process until satisfactory appliances are found.

When the user has determined that the selected dental appliances are satisfactory, the user may send one or more images indicative of the patients teeth with the selected appliances applied to the teeth to the clinic 22 and request confirmation of the selection from the dentist. Information regarding the patient and the determined appliances are then sent over the communications medium to one of the appliance service centers 23. The dentist may specify to which one of the dental labs 26 the information is to be sent. Each dental lab includes equipment for manufacturing custom made dental appliances such as brackets, archwires, etc. The appliance service center 23 then manufactures the determined appliances, and dispatches the appliances to the clinic 22.

Figure 9:
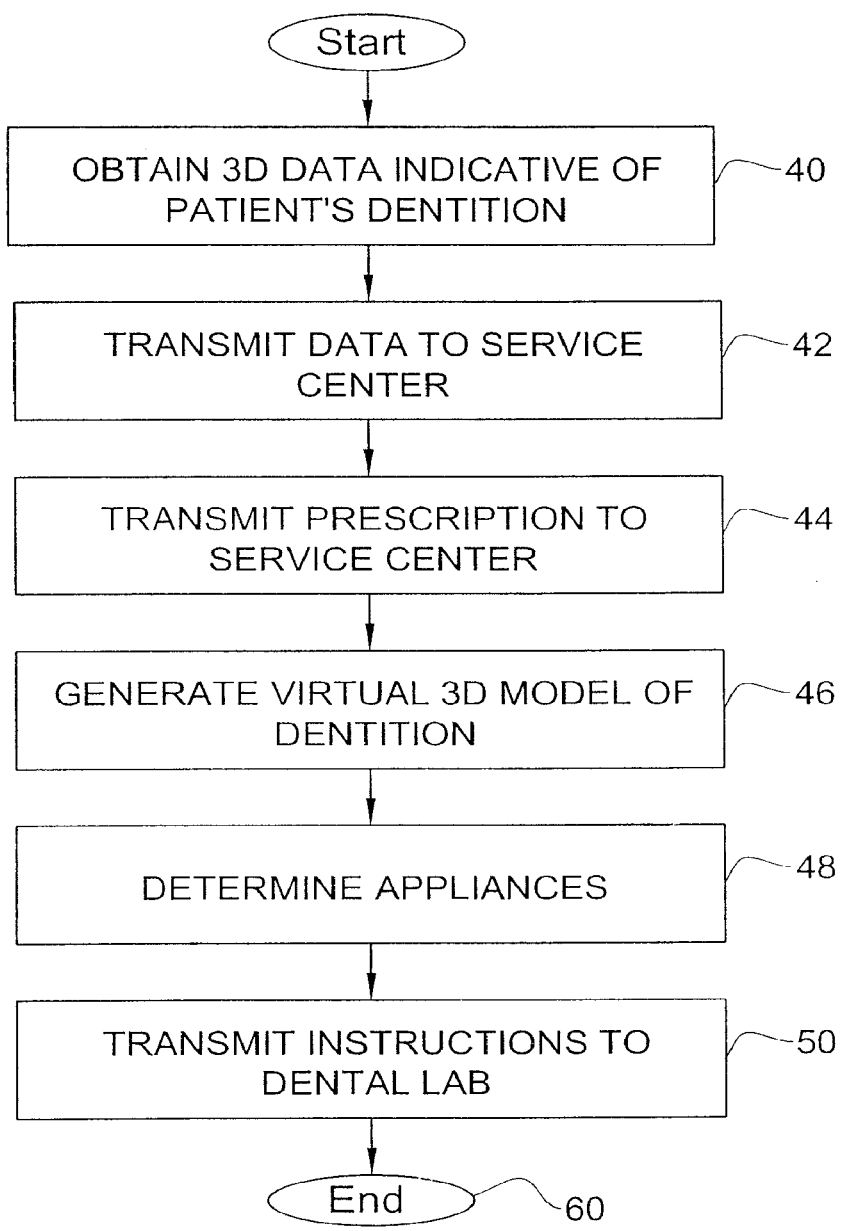
FIG. 9 shows a method for designing and producing dental appliances in accordance with a second embodiment of the invention.

FIG. 9 shows a method for designing and producing dental appliances, in accordance with another aspect of the invention. In step 40, 3D data indicative of a patient's dentition are acquired. As explained above, the data may be acquired either by scanning the patient's teeth directly, or by other methods such as for example scanning a physical model of the teeth. The acquired data are then transmitted to a dental service center (step 42). In step 44, a prescription is sent from a dental clinic to the service center specifying the teeth that are to be moved in a dental treatment, as well as the final position of the teeth at the conclusion of the treatment. Then, in step 46, the service center executes computer software to generate from the acquired data a virtual 3D model of the patient's dentition. The virtual model is used to determine the dental appliances that are required to execute the dental treatment specified in the prescription (step 48). Finally, in step 50, a list of the determined appliances is transmitted to a dental lab 26 where the appliances are made.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for manufacturing a dental prosthesis, the method comprising:
    receiving three dimensional data indicative of a patient's oral cavity;
    generating, based on the three dimensional data, a dentition model that includes a prosthesis preparation and external surface shape geometry of a prosthesis coupling portion of the preparation;
    generating, based on the dentition model, prosthesis data comprising three dimensional shape data of a first portion of the dental prosthesis, the first portion being an internal part of the dental prosthesis and including an inner surface of the dental prosthesis, the three dimensional shape data of the first portion including a preparation coupling portion of the dental prosthesis that is configured for coupling the first portion of the dental prosthesis and the preparation, the prosthesis data further comprising three dimensional shape data of an outer surface of the first portion of the dental prosthesis;
    fabricating the first portion of the dental prosthesis based on the prosthesis data; and
    transmitting data for manufacture of a second portion of the dental prosthesis, the second portion being configured to couple with the first portion, the transmitted data including at least one of: 1) three dimensional shape data of the outer surface of the first portion, and 2) three dimensional shape data of an inner surface of the second portion that is configured for coupling the second portion and the first portion.

2. The method of claim 1, wherein a dimensional accuracy used for fabricating the inner surface of the first portion is equal to or less than about 40 microns.

3. The method of claim 1, wherein a dimensional accuracy used for fabricating the inner and outer surfaces of the first portion is equal to or less than about 40 microns.

4. The method of claim 1, wherein the first portion comprises a prosthesis coping.

5. The method of claim 1, wherein the three dimensional data indicative of a patient's oral cavity is received over an electronic communication network.

6. The method of claim 1, wherein the data for manufacture of the second portion is transmitted over an electronic communication network to a dental service lab.

7. The method of claim 1, wherein the generated prosthesis data comprises three dimensional shape data of the inner surface and an outer surface of the second portion of the dental prosthesis.

8. The method of claim 1, wherein the three dimensional data indicative of a patient's oral cavity is generated at a dental clinic.

9. A method for manufacturing a dental prosthesis, the method comprising:
    receiving three dimensional data indicative of a patient's oral cavity;
    generating, based on the three dimensional data, a dentition model that includes a prosthesis preparation and external surface shape geometry of a prosthesis coupling portion of the preparation;
    generating, based on the dentition model, first portion prosthesis data comprising three dimensional shape data of a first portion of the dental prosthesis, the first portion being an internal part of the dental prosthesis and including an inner surface of the dental prosthesis, the first portion prosthesis data including three dimensional shape data of a preparation coupling portion of the dental prosthesis that is configured for coupling the first portion of the dental prosthesis and the preparation, the first portion prosthesis data further comprising three dimensional shape data of an outer surface of the first portion of the dental prosthesis;
    transmitting the first portion prosthesis data to a dental service center for manufacture of the first portion of the dental prosthesis; and
    fabricating a second portion of the dental prosthesis, the second portion being an external part of the dental prosthesis and having an external surface of the dental prosthesis, the second portion of the dental prosthesis being configured to couple with the first portion of the dental prosthesis.

10. The method of claim 9, wherein a dimensional accuracy used for fabricating the inner surface of the first portion is equal to or less than about 40 microns.

11. The method of claim 9, wherein a dimensional accuracy used for fabricating the inner and outer surfaces of the first portion is equal to or less than about 40 microns.

12. The method of claim 9, wherein the first portion comprises a prosthesis coping.

13. The method of claim 9, wherein the three dimensional data indicative of a patient's oral cavity is received over an electronic communication network.

14. The method of claim 9, wherein the prosthesis data for manufacture of the second portion is transmitted over an electronic communication network to a dental service lab.

15. The method of claim 9, wherein the generated prosthesis data comprises three dimensional shape data of the inner surface and an outer surface of the second portion of the dental prosthesis.

16. The method of claim 9, wherein the three dimensional data indicative of a patient's oral cavity is generated at a dental clinic.

17. The method of claim 9, wherein fabricating the second portion of the dental prosthesis comprises:
    receiving the first portion of the dental prosthesis; and
    applying a first material layer directly to the first portion.

18. The method of claim 17, further comprising:
obtaining three dimensional shape data of an as-applied external surface of the first material layer; and
using the three dimensional shape data of the first material layer as-applied external surface to generate first machining paths for a material removal operation configured to produce a predefined desired external surface of the first material layer, the first machining paths being tailored to the first material layer as-applied external surface to reduce machining times as compared to comparable machining paths suitable for a fictitious external surface envelope for the first material layer.

19. The method of claim 18, further comprising:
applying a second material layer directly to the first material layer;
obtaining three dimensional shape data of an as-applied external surface of the second material layer; and
using the three dimensional shape data of the second material layer as-applied external surface to generate second machining paths for a material removal operation configured to produce a predefined desired external surface of the second material layer, the second machining paths being tailored to the second material layer as-applied external surface to reduce machining times as compared to comparable machining paths suitable for a fictitious external surface envelope for the second material layer.

20. The method of claim 9, wherein fabricating the second portion of the dental prosthesis comprises:
receiving the first portion of the dental prosthesis;
mounting the first portion to a holding fixture;
scanning the inner surface of the first portion to generate three dimensional surface data of the first portion inner surface;
applying a first material layer directly to the first portion;
using the three dimensional surface data of the first portion inner surface to adjust material removal instructions used to form an external surface of the first material layer to produce a desired alignment between the first material layer external surface and the first portion inner surface.

* * * * *